United States Patent [19]

Falat

[11] Patent Number: 4,869,874
[45] Date of Patent: Sep. 26, 1989

[54] ATMOSPHERIC CORROSIVITY MONITOR

[75] Inventor: Ladislav Falat, College Park, Md.

[73] Assignee: Westvaco Corporation, New York, N.Y.

[21] Appl. No.: 143,517

[22] Filed: Jan. 13, 1988

[51] Int. Cl.⁴ .......................................... G01N 17/00
[52] U.S. Cl. .................................. 422/53; 73/336.5; 338/35; 364/550; 364/557; 422/98
[58] Field of Search ...................... 338/35; 422/53, 58, 422/98; 73/489, 336.5; 364/550, 556, 557; 23/254

[56] References Cited

U.S. PATENT DOCUMENTS

| | | | |
|---|---|---|---|
| 3,578,409 | 5/1971 | Silverman et al. | 23/254 |
| 4,114,450 | 9/1978 | Shulman et al. | 73/489 |
| 4,503,707 | 3/1985 | Rosa et al. | 73/336.5 |
| 4,642,782 | 2/1987 | Kemper et al. | 364/550 |
| 4,745,564 | 5/1988 | Tennes et al. | 364/566 |

FOREIGN PATENT DOCUMENTS 0832568  5/1981  U.S.S.R. ................... 422/53

Primary Examiner—Barry S. Richman
Assistant Examiner—Marcella Iris Fruchter

[57] ABSTRACT

A portable, environmental monitoring apparatus comprising a self-contained and internally powered data acquisition and recording device for continuously monitoring the environmental conditions in an enclosed space, preferably a computer control room. The apparatus includes sensors which measure pressure, temperature, relative humidity and the corrosive nature of the environment. The signals generated by the sensors and the atmospheric corrosion indicators are stored in a memory module included in the circuitry of the recording device. The memory module interfaces with an IBM-type PC for off loading the data and storing it on a floppy disc.

8 Claims, 2 Drawing Sheets

ATMOSPHERIC CORROSIVITY MONITOR

BACKGROUND OF THE INVENTION

The present invention relates to the measurement of indoor atmospheric corrosivity particularly with respect to its harmful characteristics on electronic equipment. Pulp Mills, Oil Refineries and other related industries generate corrosive gases which are harmful to the circuitry in electronic equipment. Such gases include sulfur dioxide, hydrogen sulfide, hydrogen chloride and chlorine dioxide for example. These gases even at parts-per-billion concentrations, which are far below what is permissible for humans, can lead to the failure of computer control equipment due to corrosion of circuitry in as little time as several months, depending upon the corrosive gas concentration, temperature and humidity. Because of the potential of costly down time from such failures, and safety concerns, industries are spending millions of dollars each year purifying computer control room atmospheres and measuring the corrosivity of such atmospheres.

At the present time, the standard industry method for measuring the corrosivity of the atmosphere in a computer control room is to expose a clean copper strip to the atmosphere for 1-3 months, and subsequently determine the amount of corrosion product developed by electrochemically converting the oxidized copper back to metallic copper. By measuring the amount of electrical charge needed for the above conversion, the amount of copper that corroded in the time period of exposure can be calculated. The disadvantage of this method is that it is labor intensive and requires costly analysis and measurement of the corrosion products after the exposure period. Obviously it would be far preferable to have available a monitoring device which would enable one to measure and record the corrosivity of the atmosphere continuously and to relate the corrosivity to as many variables as possible.

In the present invention, the atmospheric monitoring device is self contained and powered. The device includes sensors for temperature, relative humidity, pressure and corrosion indicators. These sensors sense atmospheric conditions and generate inputs to a microprocessor. The microprocessor scans the signals generated and records in a memory module excursions from set conditions which last for more than a designated time period. The result is an integrated record of the atmospheric conditions monitored on a time zero scale. Spurious momentary changes in conditions are ignored, but a full history of both regular and irregular excursions from a set of specified conditions is recorded.

Related prior art in the general area of the present invention includes U.S. Pat. Nos. 4,114,450 and 4,503,707. In the first patent, a self contained and internally powered shock, temperature and relative humidity acquisition and recording device is disclosed. In the latter patent, a hygrometry probe is disclosed for sensing moisture, temperature and pressure, linearizing the moisture measurement, and providing a digital output indicative of the linearized moisture, temperature and pressure.

SUMMARY OF INVENTION

The present invention is directed to a self contained atmospheric monitoring device which provides time dependent information about the environment in which it is located. The essential elements of the monitoring device include a sensor board, a microprocessor board and a removable self-powered memory module. The sensor board includes a plurality of environmental sensors including one or more atmospheric corrosion indicators and temperature, pressure and relative humidity probes. The output channels of the sensor board provide signals to the microprocessor responsive to changes in the atmosphere being monitored as detected by the corrosive indicators and environmental probes. The signals provided in analog format are fed to resistance comparators. The comparators convert the analog signals to binary output signals representing atmospheric changes detected by the various probes. In the preferred embodiment, the outputs from the relative humidity and pressure probes are received directly by the microprocessor as binary signals since these probes are preferably of the switch-type (i.e., open or closed).

The microprocessor scans the channels several times each second. The signals in the channels for relative humidity, pressure and temperature reflect changes in atmospheric conditions which deviate from pre-set conditions. The pre-set conditions may be incorporated in the sensors which generate binary signals or incorporated in comparators for sensors which generate analog signals. If a change in state of any channel is detected, a timer is started for that channel. If the new state remains for longer than a prescribed time period (i.e., on the order of about 300 seconds), the change in state is recorded in the memory module as well as the time elapsed since time zero when the monitoring device was first activated. Meanwhile, the atmospheric corrosion indicators are preferably in the form of fuses and comprise thin films of a material sensitive to corrosive atmospheres such as copper, silver or the like. These materials are preferably vapor deposited or otherwise applied to substrates mounted on the sensor board. The films are preferably of different thicknesses in increments on the order of about 200, 500, 750 and 1,000 Angstroms. Leads are provided for each corrosion indicator for measuring the resistance of each film thickness. As the films corrode, the resistances between the leads increase and the corrosion indicators behave as switches going from an essentially closed to an open condition. The open condition is pre-defined in the resistance comparator by a specified resistance chosen to represent the open condition. Thus, the microprocessor receives an input from each corrosion indicator as a binary signal when the resistance of each corrosion indicator reaches the predetermined set point. These signals are recorded in the memory module as the elapsed time since the monitoring device was activated (time zero).

At the end of a designated period of time (usually on the order of about six months), the memory module is removed from the monitoring device and the contents are downloaded to a computer for analysis. The record obtained from the memory documents the time it took for each corrosion indicator fuse to reach its open circuit condition, and the changes in state of each of the other environmental conditions which occurred after the monitoring device was activated and which remained in effect for the designated time period. With this information, the effect of excursions in temperature, pressure and relative humidity can be correlated with the rate of corrosion of the corrosion indicators and both regular and irregular excursions in temperature, pressure and relative humidity can be documented. These data yield an integrated corrosion rate and hence a measure of the corrosivity of the atmosphere being monitored, thus enabling one to make corrections as needed.

DETAILED DESCRIPTION

Figure 1:
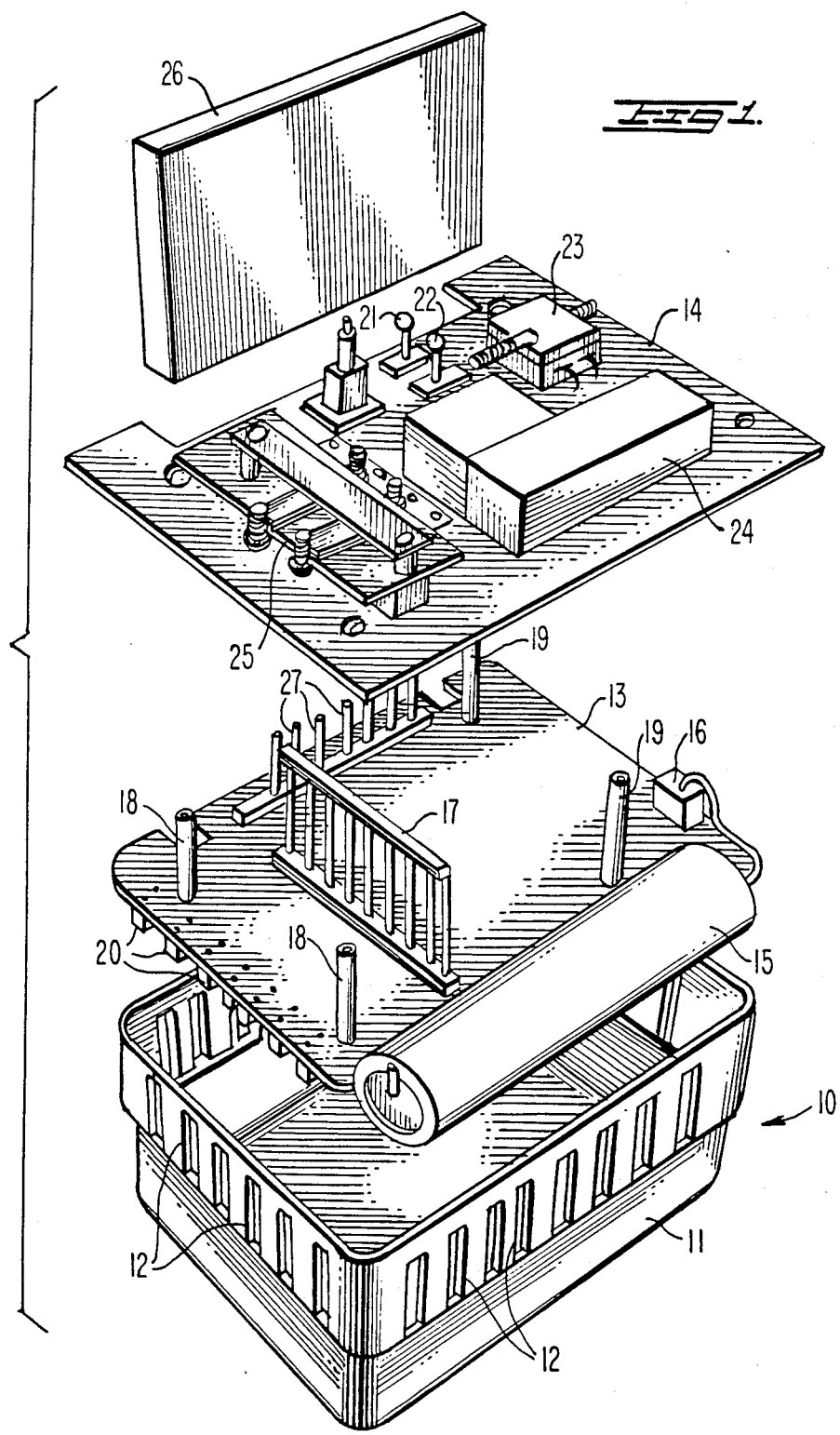
FIG. 1 is an expanded view showing in perspective the different elements of the environmental monitoring device of the present invention; and, FIG. 2 is a schematic diagram showing the relationship between the various working elements of the device.

Referring now to the drawings, FIG. 1 is an expanded view of the apparatus of the present invention with reference numeral 10 denoting a box-like case or housing consisting of a cover section 11 and a base member (not shown). The cover section 11 houses all of the components of the subject apparatus and is preferably made of a plastic material with openings 12 for exposing the components to the environment desired to be monitored. The base member (not shown) is adapted to be mounted on a wall or another surface in the enclosed area to be monitored, and the housing 11 containing the components is fixed to the base member in any suitable manner.

The primary components of the monitoring apparatus comprise a sensor board 14 and microprocessor board 13 which may be fixedly attached to the housing cover 11 in any suitable manner, and a removable self powered memory module 26. The circuit boards are preferably of the plug-in type for easy replacement when desired. The microprocessor board 13 includes a power cell 15 in the form of a long life battery. The preferred battery has a life of from between about six months to one year. The power cell 15 provides the necessary energy for operating a plurality of environmental sensors, including one or more atmospheric corrosion indicators, and temperature, pressure and relative humidity probes, as well as other electronic circuitry including the sensor and memory modules. The power cell 15 is attached to the circuitry of microprocessor board 13 via a plug-in connector 16 and the circuitry of microprocessor board 13 is connected to the circuitry of the sensor board 14 via pin connectors 17. The two circuit boards 13 and 14 are kept separated from one another by struts 18 and 19. Also included on microprocessor board 13 are a plurality of low power, high efficiency LED indicators 20 for designating power "on", and out of specification of the channels for the corrosion indicators and the other environmental probes. In a preferred format the processor module may comprise a NEC 7500 processor, 2764 EPROM (or PROM), and 74373 associated drivers/buffers.

Sensor board 14 contains a pair of thermistors 21, 22 which serve as temperature probes, a pressure differential switch 23, a humidity sensor 24, space for a plurality of corrosion indicators generally designated at 25, and a standard atmospheric corrosion coupon 28. Sensor board 14 includes a cut out in the rear to provide space for the memory module (RAM) 26 which plugs into the circuitry of circuit board 13 via male access pins 27. The RAM module 26 is preferably constructed on a printed circuit board with a 36 pin female edge card connector. It may be wired for four 8K RAM chips or a single 32K RAM chip could be used. The memory module 26 preferably contains a secondary battery memory backup to retain the recorded data during transportation before it is offloaded onto the floppy disc of a computer. For this purpose, the RAM module 26 is designed to interface with, and run on, an IBM-PC, PC-XT, PC-AT or any IBM compatible computer. The interface card is preferably designed to accept the RAM Module 26 without removal of the RAM card from its housing. Alternatively, an interface module to which the RAM module 26 connects may be made by one skilled in the art, to connect by ribbon cable to the interface card. The data acquisition module is designed to continuously check the circuit state of at least eight channels. It is designed to store in a temporary register the time since "time zero" i.e., when the monitor is first activated, at which a change of state in any of the eight inputs occurs. If that change remains in affect for longer than a preselected time (preferably about 300 seconds), it will record the change of state time, the sensor number and the circuit state in the memory module 26.

Prior to discussing the signal flow of the outputs from the various sensors, the method of operation of such sensors and preferred types of sensors are disclosed and described. The temperature sensors 21, 22, are of the analog type. Meanwhile, the pressure differential sensor 23 and humidity sensor 24 are preferably of the switch type. That is, they will switch from an open circuit to a closed circuit state (or vice versa) when a specified condition becomes abnormal. These sensors will then return to the original circuit state when conditions return to the normal state as defined by a specified condition. Two temperature sensors 21, 22 are preferred. Thermistors manufactured for example by Fenwall Company and identified by part no. UVT51J1 may be used. One temperature sensor is preferably set to change its circuit state when the temperature reaches 78 degrees F. ($\pm$ 1 deg. F.) and the other will change its circuit state when the temperature lowers to 68 degrees F. ($\pm$ 1 deg. F.).

The humidity probe 24 is of the polystyrene film type, manufactured for example by Honeywell Corporation, and identified by part no. H46A1509. The circuit state of probe 24 is preferably set to change when the relative humidity exceeds a pre-set condition of 55% ($\pm$ 5%), and to return to its original state when the relative humidity returns to the range specified.

The pressure differential probe is of the diaphrag type, manufactured for example by Micro Pneumatic Logic, Inc., and identified as part no. X02616-3-501. The circuit state of this probe will change when the differential pressure falls below 0.08 ($\pm$ 0.03) inches of water, and will return to its original state when the pressure returns to a point within the specified condition.

In addition to the sensors described above, sensor board 14 also includes a plurality of corrosion indicators mounted on card 25, and a standard corrosion coupon 28. The corrosion indicators are preferably of the fuse-type comprising thin films of copper or another corrosion sensitive material, vapor deposited on substrates of generally rectangular shape. The thicknesses of the films deposited on the substrates may vary depending upon the application, but they are generally on the order of increments such as 200, 500, 750 and 1,000 Angstroms. The substrates are preferably clear glass on the order of about 0.060 inch thick with dimensions of about 0.50 to 1.5 inches in width and length. Each corrosion indicator is provided with leads for connection to the circuitry of the sensor board 14. As the corrosion sensitive films corrode, the resistances between the leads increases. As the film thickness of any corrosion indicator is converted to a corrosion product, the resistance of that sensor increases in a non-linear manner. Thus a specific resistance value is preselected as the point where the corrosion indicator is deemed to be fully corroded. When this point is reached, the corrosion indicator behaves as a switch, going from an essentially closed to an essentially open circuit condition. These switch on and off conditions are stored in the memory module 26 on a time zero scale so that one can tell how long it took for a given corrosion indicator to be fully corroded. Thus the corrosivity of the atmosphere to which the corrosion indicators are exposed can be characterized in real time with no need for subsequent analysis.

Figure 2:
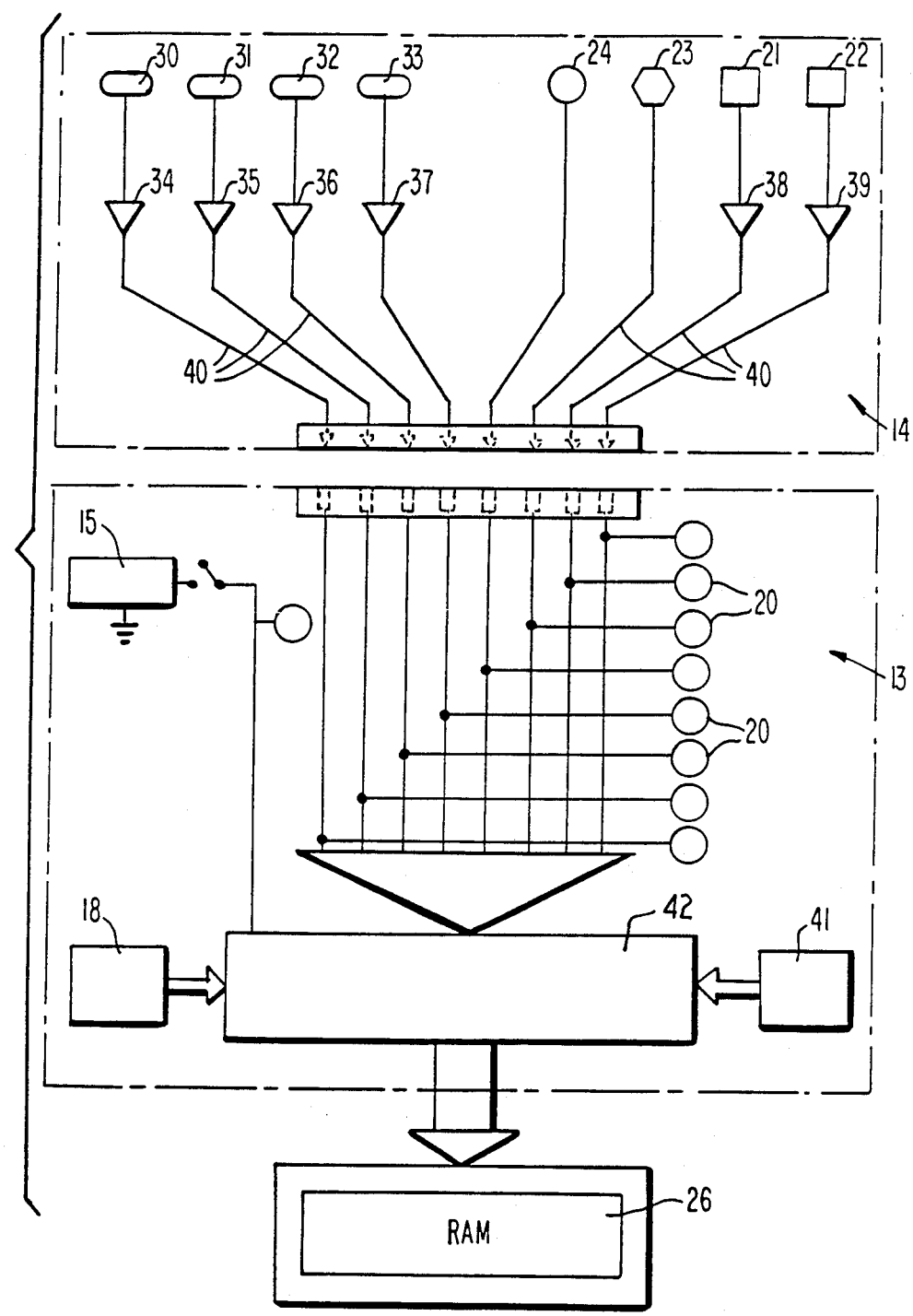

The purpose of the circuitry associated with the sensors is to convert the outputs into a format which is easily handled by digital electronics. Accordingly, the exact magnitude of the changes in conditions is not determined, but rather an event is classified into one of a predetermined number of amplitude windows or ranges within a predetermined range of values. Referring now briefly to FIG. 2, the circuit is represented by three modules, sensor board 14, microprocessor board 13 and the removable, self powered memory module 26. Circuitry on the sensor board 14 converts analog signals from the thermisters 21, 22 and the corrosion indicators 30, 31, 32, 33 into digital (binary) signals. This is accomplished by resistance comparators 34–37 and 38, 39 which change their output from high to low (and vice versa), when the signal from its attached sensor remains in effect for the designated period. The pressure and relative humidity sensors 23, 24 are preferably of the switch-type, thus providing a binary signal without the need for resistance comparators. It will be understood by those skilled in the art that depending upon the type of sensors used comparators may or may not be required to produce a binary signal.

In the embodiment illustrated in FIG. 2, eight sensors are disclosed which direct their signals through channels 40. The output from the channels 40 of sensor board 14 act as inputs to the microprocessor board 13. Low power LED's 20 are incorporated into the microprocessor board to indicate the real time state of each channel.

The microprocessor 42 scans each channel 40 several times each second. If it detects a change of state of any one channel (from low to high or vice versa), a timer in clock circuit 41 is started for that channel. If the new state remains for longer than a specified time period (preferably on the order of about 300 seconds), the change of state of that channel 40 is recorded in the memory module 26 as well as an elapsed time (less 300 seconds) since time zero, that the change of state occurred. Thus, spurious or momentary changes in state of the channels are not permanently recorded.

At the end of a designated interval (on the order of about six months), the memory module 26 is removed from the monitoring apparatus and its contents downloaded to an IBM-PC or compatible through a suitable interface module. A record can then be reproduced from the memory contents documenting when during the sampling period, changes in state of each channel 40 occurred, corresponding to relative humidity, pressure and temperature excursions, for the monitored location. The elapsed time indicating when the corrosion indicators 31–33 became fully corroded, together with the thickness remaining of the vapor deposited corrosion sensitive material define an integrated corrosion rate, thus yielding the corrosivity of the atmosphere in the monitored location and thus allowing one to make corrections to those conditions.

What has been shown and described is an atmospheric monitoring device programmed to yield an accurate representation of the corrosivity of the atmosphere of a monitored location over a period of time, with real time entries of excursions in temperature, pressure and relative humidity during that period. This information enables one to correlate any influences on the corrosion rate with excursions in temperature, pressure and relative humidity. Accordingly, while there has been shown and described what is considered to be the preferred embodiment, further modifications thereto will readily occur to those skilled in the art. It is to be understood that the invention should not be limited to the specific arrangement and types of elements described, but all equivalents, alterations and modifications coming within the spirit and scope of the appended claims are intended to be included.

What is claimed is:

1. In combination an enclosed space, an apparatus for monitoring and recording the environmental conditions existing in said enclosed space, a case for housing said apparatus, and means for mounting said case in said enclosed space, wherein said case includes openings for exposing said apparatus to the environmental conditions existing in said enclosed space and wherein said apparatus comprises:
   (a) a plurality of environmental data sensors located on a sensor board mounted in said case and adapted to be responsive to changes in temperature, relative humidity and atmospheric pressure occurring in said enclosed space;
   (b) a microprocessor circuit coupled to said data sensors for scanning signals from said data sensors and recording those signals which deviate from pre-set conditions and which remain in effect for a prescribed period of time; and,
   (c) a digital memory device coupled to said microprocessor circuit for collecting and storing recorded signals from said microprocessor circuit on a time zero basis.

2. The combination of claim 1 wherein the sensor board includes a plurality of corrosion sensors comprising fuse-type indicators consisting of inert substrates applied with thin films of corrosion sensitive material in thickness increments of about 200, 500, 750 and 1,000 Angstroms, said corrosion sensors being coupled to said microprocessor circuit where signals from said corrosion sensors are detected and recorded.

3. The combination of claim 2 wherein said microprocessor circuit includes means for recording signals from said corrosion sensors on a time zero basis when each corrosion sensor reaches a specified resistance established by a predetermined set point.

4. The combination of claim 1 wherein the enclosed space is a computer control room.

5. In combination, a computer control room, an apparatus for monitoring and recording the environmental conditions existing in said computer control room, and a case for housing said apparatus mounted in said computer control room, wherein said case includes openings for exposing said apparatus to the environmental conditions existing in said enclosed space and wherein said apparatus comprises:
   (a) a plurality of environmental data sensors located on a sensor board mounted in said case and adapted to be responsive to changes in temperature, relative humidity and atmospheric pressure occurring in said control room and wherein said plurality of environmental data sensors includes a plurality of corrosion sensors adapted to be responsive to the corrosive nature of the environment in said control room;

(b) a microprocessor circuit coupled to said data sensors for scanning signals generated by said data sensors and comparing such signals from said temperature, relative humidity and atmospheric pressure sensors with pre-set conditions over a prescribed period of time before recording an out-of-condition change sensed by one of those sensors; and, (c) a digital memory device coupled to said microprocessor circuit for collecting and storing recorded signals from said microprocessor circuit on a time zero basis.

6. The combination of claim 5:

(a) the corrosion sensors comprise fuse-type indicators consisting essentially of thin films of a corrosion sensitive material applied to inert substrates in varying thickness and wherein said apparatus further comprises:

(b) electrical leads fixedly attached to each corrosion sensor and means for applying a voltage across each corrosion sensor; and, (c) a resistance comparator connected to each corrosion sensor for providing a digital signal when the resistance of any corrosion sensor reaches a specified resistance established by a predetermined set point, and wherein the microprocessor circuit includes means for recording signals from the corrosion sensors and the digital memory device includes means for storing signals from the corrosion sensors.

7. The combination of claim 6 wherein the thin films of corrosion sensitive material comprise vapor deposited films of copper applied to a glass substrate.

8. The combination of claim 7 wherein the copper films are applied in thickness increments of about 200, 500, 750 and 1,000 Angstroms.

* * * * *